United States Patent
Arias Espinoza et al.

(10) Patent No.: US 9,829,473 B2
(45) Date of Patent: Nov. 28, 2017

(54) FLUORESCENCE DETECTOR SYSTEM FOR DETECTION OF AN AROMATIC HYDROCARBON

(71) Applicant: Nederlandse Organisatie voor toegepast-natuurwetenschappelijk Onderzoek TNO, The Hague (NL)

(72) Inventors: Juan Diego Arias Espinoza, The Hague (NL); Edsger Constant Pieter Smits, The Hague (NL)

(73) Assignee: NEDERLANDSE ORGANISATIE VOOR TOEGEPAST- NATUURWETENSCHAPPELIJK ONDERZOEK TNO, The Hague (NL)

(*) Notice: Subject to any disclaimer, the term of this patent is extended or adjusted under 35 U.S.C. 154(b) by 0 days.

(21) Appl. No.: 14/650,840

(22) PCT Filed: Dec. 13, 2013

(86) PCT No.: PCT/NL2013/050900
§ 371 (c)(1),
(2) Date: Jun. 9, 2015

(87) PCT Pub. No.: WO2014/092576
PCT Pub. Date: Jun. 19, 2014

(65) Prior Publication Data
US 2015/0330959 A1 Nov. 19, 2015

(30) Foreign Application Priority Data
Dec. 13, 2012 (EP) .................................... 12196960

(51) Int. Cl.
G01N 21/64 (2006.01)
G01N 33/00 (2006.01)
C08K 7/26 (2006.01)
G01N 21/77 (2006.01)

(52) U.S. Cl.
CPC .......... G01N 33/0047 (2013.01); C08K 7/26 (2013.01); G01N 21/64 (2013.01); G01N 21/643 (2013.01); G01N 2021/775 (2013.01); G01N 2021/7786 (2013.01); Y10T 436/212 (2015.01)

(58) Field of Classification Search
CPC ...................................................... G01N 21/64
USPC ...................................... 436/140, 172, 181
See application file for complete search history.

(56) References Cited

U.S. PATENT DOCUMENTS

| 5,244,813 | A | * | 9/1993 | Walt | ................... | G01N 21/7703 |
| | | | | | | 385/12 |
| 5,922,612 | A | * | 7/1999 | Alder | ................... | C07D 311/78 |
| | | | | | | 436/163 |
| 7,682,564 | B2 | * | 3/2010 | Ueno | ....................... | B01J 20/10 |
| | | | | | | 422/500 |
| 7,955,861 | B2 | * | 6/2011 | Fraser | .................... | C09B 57/10 |
| | | | | | | 436/127 |

OTHER PUBLICATIONS

Chow, Y. L. et al, Journal of Physical Chemistry 1995, 99, 17566-17572.*
Petrochenkova, N. V. et al, Russian Journal of Coordination Chemistry 2001, 27, 676-679.*
Karasev, V. E. et al, Russian Journal of Coordination Chemistry 2001, 27, 746-750.*
Zhang, G. et al, Journal of the American Chemical Society 2007, 129, 8942-8943.*
Banet, P. et al, Sensors and Actuators B 2008, 130, 1-8.*
Zhang, G. et al, Advanced Materials 2008, 20, 2099-2104.*
Kadir, R. et al, Environmental Science Technology 2009, 43, 5113-5116.*
Zhang, G. et al, Macromolecules 2009, 42, 8627-8633.*
Sazhnikov, V. A. et al, Doklady Physical Chemistry 2011, 437, 35-37.*
Alfimov, M. et al, "Emissive Exciplexes of Surface-Immobilized Dybenzoylmethanatoboron Difluoride with Gaseous Benzene, Toluene and Xylenes" 14th International Meeting on Chemical Sensors, Proceedings 2012, 444-447.*
Arias Espinoza, J. D. et al, "Flexible optical chemical sensor platform for BTX" 14th International Meeting on Chemical Sensors, Proceedings 2012, 655-658.*
Arias Espinoza, J. D. et al, Procedia Engineering 2012, 47, 607-610.*
McGlashan, G. S. et al, Nature 398, 792-794.*
Guo, F. et al, Macromolecules 2008, 41, 1486-1493.*
Zhang, G. et al, Macromolecules 2009, 42, 3162-3169.*
Pilla, P. et al, Sensors 2009, 9, 9816-9857.*
Aziz, F. et al, Separation and Purification Technology 2010, 73, 421-428.*
Zhang, G. et al, Applied Materials & Interfaces 2010, 2, 3069-3074.*
Xu, J. et al, Macromolecules 2011, 44, 7445-7450.*

(Continued)

*Primary Examiner* — Arlen Soderquist
(74) *Attorney, Agent, or Firm* — Morrison & Foerster LLP (57) ABSTRACT

The invention relates to a detector system suitable for detection of an aromatic hydrocarbon, comprising an organic polymeric sensor material that is permeable to the aromatic hydrocarbon, the sensor material comprising a molecular probe selected from the group of methanatoboron moieties. Further, the invention relates to the use of a detector system according to the invention for the detection of an aromatic hydrocarbon, preferably an aromatic hydrocarbon selected from the group of benzene, toluene and xylene.

23 Claims, 6 Drawing Sheets

(56) References Cited

OTHER PUBLICATIONS

Chow et al., "Molecular interactions of dibenzoylmethanatoboron difluoride ($DBMBF_2$) in the excited and ground states in solution," J. Photochem. Photobiol. A: Chem. (1991) 57:247-255.

International Search Report for PCT/NL2013/050900, dated Mar. 13, 2014, 2 pages.

Sakai et al., "White light emission from a single component system: remarkable concentration effects on the fluorescence of 1,3-diaroylmethanatoboron difluoride," Tetrahedron Letters (2012) 53:4138-4141.

Sazhnikov et al., "Silica Nanoparticles with Covalently Attached Fluorophore as Selective Analyte-Responsive Supramolecular Chemoreceptors," Nanotechnologies in Russia (2012) 7(1-2):6-14.

Truong et al., "Exciplexes or ground state complexes of (dibenzoylmethanato)boron difluoride and benzene derivatives? A study of their optical properties revisited via liquid state investigations and structure calculations," Photochem. Photobiol. Sci. (2006) 5:686-697.

Valat et al., "Unusually strong emission from an exciplex formed between benzenoid solvents and dibenzolymethanatoboron difluoride. Formation of a triplex," Can. J. Chem. (1995) 73:1902-1913.

\* cited by examiner

FLUORESCENCE DETECTOR SYSTEM FOR DETECTION OF AN AROMATIC HYDROCARBON

CROSS-REFERENCE TO RELATED APPLICATIONS

This application is the national phase of PCT application PCT/NL2013/050900 having an international filing date of 13 Dec. 2013, which claims benefit of European patent application No. 12196960.4 filed 13 Dec. 2012. The contents of the above patent applications are incorporated by reference herein in their entirety.

THE INVENTION

The invention relates to a sensor material for the detection of an aromatic hydrocarbon, to a detection system for the detection of an aromatic hydrocarbon and to the use a sensor material for detecting an aromatic hydrocarbon. Further the invention relates to a method for preparing a sensor material for the detection of an aromatic hydrocarbon.

Aromatic hydrocarbons, such as benzene, toluene and xylenes are compounds of great social and environmental significance, being widely used in industry. However they present serious health, environmental and safety dangers. Aromatic hydrocarbons can be measured optically in various ways. However, selective measurement of these gases at low concentrations and with fast detection times is still a challenging task that involves the use of expensive bound lab equipment.

One way is to detect the analyte by UV absorption, optionally after pre-concentration of the analyte from a sample. It should be noted that UV absorption spectroscopy is relatively aspecific and limits of detection as such are typically relatively poor. Accurate detection of low levels (below ppm) generally requires a selective pre-concentration technique. For instance, EP 1 712 889 A1 relates to a benzene detecting element comprising a mesoporous silicate for detecting benzene. According to paragraph [0038], the benzene molecule can be selectively detected due to the fact that the detecting element has a particular crystalline structure and the inner portion of the so called fine pore is modified with the functional group. According to the Examples, detection with UV-spectrophotometry is possible in the ppb range, using the detecting element as a pre-concentrator. This approach requires absorption of the analyte (benzene) for an undisclosed amount of time, which analyte is later release by heating towards the optical measuring set-up. It is contemplated that the response time of the sensor is rather long.

Another approach is to provide an optical sensor for an aromatic hydrocarbon to be detected comprising an analyte-sensitive material, which can respond in contact with the analyte in one of a variety of ways. For instance, the contact may cause a change in colour, a change in fluorescent properties of the material, or a change in refractive index of the analyte-sensitive material or a change in optical path due to deformation of the analyte-sensitive material. A specific type of optical sensors makes use of fluorescent molecular probes. For instance, US 2006/0051826 relates to a porous sol-gel material, which may be used in the detection of atmospheric pollutants, e.g. benzene, toluene, ethyl benzene or xylenes. The material may contain a probe molecule, i.e. a detectable molecule capable of interacting specifically with a molecular entity and of revealing the presence of that molecular entity (in combination with suitable detection means). As examples of probe molecules dibenzoylmethanatoboron difluoride and derivatives thereof are mentioned.

However, a need remains for alternative optical sensors and methods of making optical sensors. In general, sensors that can serve as an alternative are important in analytical chemistry, as—amongst others—they can be used in a different method of analysis in order to validate results obtained by another method of analysis.

Accordingly, it is an object of the present invention to provide a novel detector system or sensor material for detecting an aromatic hydrocarbon, that may serve as an alternative to known sensors.

In particular, it is an object to provide a detector system or sensor material that has a desirable mechanical property, more in particular a mechanically flexible detector or sensor material.

It is a further object of the invention to provide a novel detector system or sensor material that is improved, in particular in that a detection system comprising the (nano-structured) sensor material is improved in that it offers at least one of the following advantages: a higher selectivity towards a specific analyte, a larger dynamic range, a higher robustness, a lower detection limit, a higher sensitivity.

The selectivity of a detection system for measuring a certain environmental condition is the extent to which the detector specifically reacts to a change in a selected environmental condition, without being affected by a change in other conditions.

The dynamic range of a sensor system is the range of a changeable quantity that can be measured with that sensor system, the limits of which range are defined by the smallest and the largest value of the changeable quantity that can be measured with that sensor system.

The accuracy of a detection system is the closeness of a reading or indication of that detection system to the actual value of the quantity being measured.

Robustness is the extent to which a detection system is resistant to changes in the detection system, influences from a specific sample and influences from the environment other than the condition, other than the changes in the condition to be measured. Accordingly, as a system is more stable, the back ground noise will be less and/or fewer artefacts will occur in the measuring signal, such a spikes, base line drift and/or base line shifts.

The detection limit is the lowest measurable change in an environmental condition. It is determined by the signal to noise ratio. In general, the detection limit for a particular substance is set at a signal to noise ratio of 2 if the noise is represented as peak to peak) or 4 if the noise is represented as the root of the mean square noise (RMS noise)).

The sensitivity of a detection system is the smallest change in a environmental condition, such as a physical or chemical parameter, that can be detected by the detection system.

It is a further object to provide a novel method for preparing a sensor material or a detection system, in particular a method that allows relatively simple manufacture, that has a good reproducibility, that is relatively labour-extensive, that allows manufacturing at a relatively large scale and/or that allows relatively easy manufacture of an optical read-out platform.

In particular, it is an object to provide a method wherein the sensor material can be applied reliably, e.g. by patterning, in a relatively simple way to a substrate for a detection system.

It has now been found that one or more of these objects are realised by providing a sensor material, a detection system, respectively a method of preparing a sensor material respectively manufacturing a detection system, wherein the sensor material is permeable, comprises a specific probe for the analyte and comprises a polymer with specific properties.

Accordingly, the present invention relates to a polymeric sensor material, in particular a nano-porous polymeric sensor material that is permeable to the aromatic hydrocarbon, the sensor material comprising a molecular probe selected from the group of methanatoboron moieties. This molecular probe has fluorescent properties, at least when contacted with a monocyclic aromatic hydrocarbon, which molecular probe may be physically dispersed in the polymeric sensor material or which may be chemically incorporated in the polymer structure of the polymeric sensor material. The polymer is which the probe is embedded (such as dispersed or chemically incorporated) is also referred to herein as the 'matrix polymer'.

Further, the invention relates to a method for preparing a sensor material according to the invention, comprising
  providing a mixture comprising one or more polymerisable compounds to be polymerised to form an organic polymer and at least one component selected from the group of removable structuring agents, such as a chemically etchable polymers, and inorganic nanoparticles;
  subjecting the mixture to polymerisation, under formation of a blend of the organic polymer and the removable structuring agent and/or inorganic nanoparticles;
  if present, thereafter removing the removable structuring agent; thereby forming a an organic polymeric material.

Further, the invention relates to a detector system suitable for detection of an aromatic hydrocarbon, comprising an organic polymeric sensor material according to the invention.

Further, the invention relates to the use of a detector system according to or a sensor material according to the invention for the detection of an aromatic hydrocarbon, preferably an aromatic hydrocarbon selected from the group of benzene, toluene and xylene.

The design of the detector system may in principle be based on any fluorescence detector system. The system generally comprises an excitation source, providing electromagnetic radiation with a suitable wavelength to excite the fluoroscent probe (such as an inorganic or organic LED, a LASER, or a deuterium lamp) a sample holder (comprising the sensor material, which can contain the analyte), and a photodetector (such as an inorganic or organic photodiode, a photomultiplier tube, a spectrometer or a CCD camera). The excitation source, sample holder and photo-detector are arranged, at least during use, in a manner allowing illumination of the sample holder with electromagnetic radiation, usually light (UV, VIS, IR), of a suitable wavelength to excite the analyte (at least when bound to a suitable fluorescent probe), whereby in the presence of the analyte a fluorescent signal is generated. The light source, sample holder and photo-detector are further arranged in a manner allowing the emitted fluorescence light to be detected by the photo-detector. In an embodiment the sensor material is a substrate for the light source and/or the photodetector. In a further embodiment, the sensor material, light source and/or photodetector may be provided on another material acting as a substrate (such as a glass or a polymeric sheet, plate, prism, foil or other structure).

Suitable designs for detector systems are generally known in the art. For example, the detection system may be based on an polymeric detection system as disclosed in WO 2005/15173, of which the contents, in particular the Figures and the description thereof, the content with respect to the light sources and the content with respect to the photodetectors are, incorporated herein by reference. Another example of a suitable detector design is shown in Proc of SPIE Vol 8439, 84390Y-(Fluorescence-based optochemical sensor on flexible foils Sandeep Kalathimekkad et al.)

In FIG. 1 the gas and sample chamber contains the sensor material.

The term "or" as used herein is defined as "and/or" unless specified otherwise.

The term "a" or "an" as used herein is defined as "at least one" unless specified otherwise.

When referring to a noun (e.g. a compound, an additive, etc.) in the singular, the plural is meant to be included.

As used herein, a 'polymer' is a substance of which the molecules, in particular organic molecules (in which case the polymer is an organic polymer), are built up at least conceptually from a plurality of monomeric units. The polymer is usually built up from at least 10 monomeric units, preferably at least 50 monomeric units, at least 100 monomeric units, or at least 250 monomeric units. The upper limit of the polymer is not particularly critical and can be, for instance, 1 000, 10 000, 50 000, or more than 50 000 monomeric units. The monomeric units may be the same (a homopolymer) or the polymer may be composed of two or more different monomers (a copolymer). A copolymer may be a random copolymer, a block copolymer, an alternating copolymer or a graft copolymer. A polymer may be branched or linear. A polymer may be cross-linked or uncrosslinked. When referring herein to a polymer of a certain type, e.g. a polyolefin, a polyimide, a polyvinylpyrrolidone (PVP), or a cellulose derivative, this is meant to include copolymers additionally comprising one or more polymeric segments of another type, e.g. when referring to PVP, copolymers of PVP and an other polymeric segment, e.g. a cellulose derivative, are meant to be included.

The term 'sensor material' is used herein for the material that is sensitive towards a qualitative or quantitative change in the presence of an aromatic hydrocarbon, by which change a change in fluorescence can be observed if illuminated with light of a suitable wavelength.

The term 'analyte' is used herein for a substance (i.e. an aromatic hydrocarbon) of which one wish to determine the presence in a medium to be tested for the presence of said substance.

The term 'nanoporous' is used herein as an adjective for a material with pore sizes under between 1-100 nm, preferably between 1-20 nm. The pore size as used herein is as determinable by the Barrett-Joyner-Halenda analysis of the desorption branch of a N2 adsorption isotherm experiments. The experimental details and calculations can be found in described in Jan Roman Paul, Detlev Fritsch, Thomas Klassen, Klaus-Viktor Peinemann. Journal of Membrane Science, 389, 343. (2012) doi:10.1016/j.memsci.2011.10.046.

The sensor material may in particular form part of an optical sensor platform. The material is particularly suitable to be provided as (part of) a miniaturised system, for instance a lab on a chip or a microreactor.

The sensor material is in particular suitable for the detection of an aromatic hydrocarbon in a gas phase, for instance air. More in particular, the detector system or sensor material of the invention is suitable for use in indoor air quality monitoring, preferably for detection of toluene and/or benzene. Further, the detector system or sensor material is in particular useful for air quality control in or near petrol stations or for use in or near petrochemical plants.

The sensor material according to the invention is particularly suitable to be provided in the form of a sensor system comprising a plurality of sensors. Herein different sensors of the system may be designed for detection of different analytes, in particular different monocyclic hydrocarbons. Thus, the system may be used for simultaneous detection of a plurality of analytes.

In general, the sensor material can be used for multiple measurements or for continuous operation if desired, due to the reversible character of the absorption of the gases in them.

The sensor material is in particular suitable for optochemical detection of a monocyclic hydrocarbon, in particular benzene, toluene or a xylene, The xylene may be o-xylene, m-xylene or p-xylene. These monocyclic hydrocarbons are herein also referred to as 'a BTX' (singular) or BTXs (plural). A detection system according to the invention can also be used for the detection of another aromatic hydrocarbon, in particular ethyl benzene or trimethyl benzene.

The optochemical detection of molecules is a widely studied field in the sensor field. However there are few materials for which the principle of detection is the fluorescence of exciplex species.

The complexity of finding a sensor material, in particular a sensor material that can be shaped in the form of a film or membrane for optochemical gas sensing lies in satisfying requirements like good compatibility between the molecular probe (and the matrix and high permeability of the gas into the matrix. It is a challenge to fulfil these requirements in particular in the case of a methanatoboron, as a molecular probe for a BTX that offers satisfactory properties for a detection system. It is in particular a challenge to provide a material in which properties like BTX solubility, inertness of the matrix material towards the molecular probe, and porosity/BTX permeability are satisfactory. In addition to these properties, and due to its application in optical sensors, the matrix preferably has to lack significant UV absorption and fluorescence, which if present, may interfere with the fluorescence of the molecular probe.

To the best of the inventors' knowledge, the present invention is the first report of a permeable and nanoporous (organic) polymer or composite material, in particular a film or membrane, provided with a fluorescent methanatoboron for the detection of a BTX. In accordance with the invention the fluorescent dye (i.e. a molecular probe of which a fluorescent property changes upon interaction with the analyte, usually a molecular probe which becomes fluorescent or has an increased fluorescence, when interacting with the analyte.) can be properly dispersed in a satisfactory high concentration without unacceptable aggregation of the dye and showing still sensing activity. The sensor material can be applied by deposition, in particular by patterning, allowing a simple integration into different optical read-out platforms, including flexible platforms.

Advantageously, the sensor material is a membrane, which is selectively permeable towards one or more BTX's, i.e. which has a lower permeability to another gas, in particular a polar gas, such as ethanol or water vapour, than to the BTX.

As used herein, the term 'mechanically flexible' or in short 'flexible' is used for products for materials that withstand bending around a roll having a diameter as low as 10 mm without breaking or other unacceptable deterioration, such as delamination of the sensor material from a substrate on which it has been deposited. Preferably, the flexible product or material should withstand over 500 bending actions around a 10 mm diameter roll, more preferably over 1500 bending actions, without unacceptable deterioration, in particular without delamination of a sensor material from a substrate.

The sensor material typically is an organic polymeric material, which means that the material at least substantially consists of one or more organic polymers. As opposed to non-organic polymers, e.g. silicon based polymers, organic polymers typically comprise a skeletal structure (e.g. a branched or non-branched chain, a crosslinked structure) having carbon atoms. The skeletal structure consists of carbon atoms or contains one or more heteroatoms in addition to carbon. The number of heteroatoms as a percentage of the total number of atoms in the skeletal structure generally is less than 50% of the atoms in the skeletal structure, and in particular less than 25% of the atoms in the skeletal structure. If present, the heteroatom(s) are preferably selected from N (e.g. polyamides) and O (e.g. polyethers, polyesters, polyamides). The organic polymer or polymers may also be referred to as the matrix polymer, as they generally provide the integral structure of the material in which optional other components are distributed. In addition the sensor material may comprise additives, such as the molecular probe (which may fully or partially be present as part of the polymer, or which may be physically dispersed in the material), a filler, a plasticizer and/or one or more other additives for polymeric materials. The organic polymer content of the sensor material usually is at least 50 wt. %, in particular at least 70 wt. %, more in particular at least 80 wt. %, even more in particular at least 85 wt. %.

The sensor material is permeable to the aromatic hydrocarbon of which the presence in a sample is to be detected. As used herein, the term permeable is in particular used for a material having a permeability at 35° C. and 1 atmosphere of at least 100000 ($cm^3$ $cm/(cm^2$ s cmHg)) in particular at least. 140000 ($cm^3$ $cm/(cm^2$ s cmHg)), as measured by constant volume-variable pressure methodology, of which the experimental details and calculations are described in Jan Roman Paul, Detlev Fritsch, Thomas Klassen, Klaus-Viktor Peinemann. *Journal of Membrane Science*, 389, 343. (2012) doi:10.1016/j.memsci.2011.10.046.

Preferably, the sensor material is more permeable for an aromatic hydrocarbon than for a polar gas, in particular more permeable for a BTX than for water and/or ethanol at 25° C.

An open-nanoporous sensor material is particularly preferred for one or more of the following reasons: a fast response time, a particularly good limit of detection, a good reversibility (i.e. the BTX can be removed effectively within an acceptable time, once the sensor material is no longer exposed to a medium containing BTX). Further, a nanoporous material is considered to be advantageous over porous material with a larger (average) pore size, in particular with respect to a favourable signal to noise ratio. Without being bound by theory the inventors contemplate that the relatively low pore size is advantageous in this respect in view of reduced scattering effects, in particular for a system based in waveguiding or fibre optics In a preferred embodiment, the pore volume of the (nanoporous) sensor material is at least 0.2 ml/g, more preferably at least 0.25. In a particular embodiment, the pore volume is 0.5 ml/g or less more in particular 0.4 ml/g or less. A relatively high BET surface area is also advantageous for good detector properties. Preferably BET surface area at least 150 m²/g, more preferably at least 200 m²/g. In a particular embodiment, BET surface area is 400 m²/g, more in particular 300 m²/g or less. As used herein, the pore volume and the BET surface area is as determined by the methodology mentioned in Seo and Hillmyer, *Science* 336, 1422-1425 (2012)

A polymer of the sensor material is generally selected to be substantially transparent in this range or at least at the intended excitation wavelength or intended excitation wavelength range, and to lack significant emission at the intended excitation wavelength (range).

Particularly good results have been realised with an acrylic polymer. Such polymer has been found to offer a good transparency to light of a suitable wavelength to allow passage of the excitation light for the methanatoboron and emitting light (fluorescent signal). Such a polymer is suitable for a detection system using light with a wavelength in the (near) UV, visible and IR range. An aliphatic acrylic polymer or an acrylic polymer substantially comprising aliphatic moieties is particular advantageous with respect to high transparency and the absence of fluorescent behaviour in the near) UV, visible and IR range.

Also it has been found possible to prepare such polymers with a good permeability towards an aromatic hydrocarbon, to prepare flexible sensor materials from such polymers, and also to have the methanatoboron moieties distributed well throughout the material without unacceptable aggregation of the methanatoboron molecules throughout the sensor material.

The inventors have in particular realised that it is advantageous to provide a copolymeric sensor material. By selecting suitable monomeric units a material is provided that can be optimised with respect to desired mechanical flexibility, distribution of the molecular probe into the sensor material, permeability into and/or solubility of the analyte in the sensor material. A copolymeric sensor material, in particular a phase-separated copolymer, is in particular advantageous for its good microstructuring properties and/or a good uniformity in the pores. The latter contributes to the reproducibility of the response between different sensor material samples.

The copolymer is typically selected from the group of random copolymers, block copolymers, alternating copolymers and graft copolymers.

In a preferred embodiment, the sensor material is at least substantially composed of a copolymer comprising a first type of monomeric units, which units are based on a monomer which improves compatibility of the sensor material with the molecular probe, or increases the permeability and solubility towards a BTX, preferably relative to the permeability to a polar gas, in particular water and/or ethanol vapour.

Preferably, the copolymer comprises a second type of monomeric units, containing one or more groups that can act as plasticizers, and more preferably, said monomeric units spread polymer chains apart, reducing chain packaging. This is in particular advantageous for improved permeability of the analyte, and has a positive effect on response time and/or detection limit.

The monomeric units of the first type preferably have a high affinity for non-polar solvents, compared to the monomeric units of the second type. The monomeric of the first type are preferably aliphatic (and different from the monomer of the second type). Preferably, the monomeric units of the first type are based on an acrylic or methacrylic aliphatic monomer. Hereinafter, the term (meth)acrylic is used as an abbreviation for the phrase 'acrylic or methacrylic', the term (meth)acrylate is used as an abbreviation for the phrase 'acrylate or methacrylate'. A copolymer comprising (meth)acrylic units is considered advantageous in particular in order to increase solubility of analyte.

Alkyl (meth)acrylates are in particular preferred monomeric units of the first type for improving selectively the permeability for a BTX relative to the permeability for a polar gas, such as water or ethanol vapour. Particularly suitable are C2-C18 alkyl (meth)acrylates, more in particular C6-C18 alkyl (meth)acrylates. Particularly preferred is an alkyl acrylate selected from the group of n-hexyl acrylate, n-heptyl acrylate, n-octyl acrylate, isooctyl acrylate, n-nonyl acrylate, isodecyl acrylate, lauryl acrylate, myristyl acrylate, stearic acrylate. If monomeric units of the first type are present in the copolymer, usually at least 10 wt % of the copolymer, preferably 10-60 wt. %, more preferably 30-50 wt. % of the copolymer is (at least conceptually) based on the monomeric units of the first type.

In a specifically preferred embodiments, a monomeric unit of the second type is based on a monomer, in particular a (meth)acrylic monomer, that would form a rubbery homopolymer, when homopolymerised. The term 'rubbery homopolymers' is used herein for polymers with a glass transition lower than ambient temperature (25° C.), in particular lower than 10° C.; Tg is as determined by differential scanning calorimetry (DSC), placing 10 mg sample in a crucible and heating at a rate of 10° C./min under nitrogen atmosphere.

More preferably, monomeric units of the second type are based on a monomer selected from the group of tetrahydrofurfuryl acrylate, di(ethylene glycol) ethyl ether acrylate, 3,5,5-Trimethylhexyl acrylate, Benzyl 2-propylacrylate, 4-tert-Butylcyclohexyl acrylate, Ethylene glycol phenyl ether acrylate, Additional methacrylate monomers can be used, including Cyclohexyl methacrylate, Tetrahydrofurfuryl methacrylate, Phenyl methacrylate, 3,3,5-Trimethylcyclohexyl methacrylate. In a further embodiment, monomers of the second type include styrene or functionalized styrene monomers, preferably selected from the group 4-Benzyloxy-3-methoxystyrene, 4-tert-Butylstyrene, Chlorostyrene, Methylstyrene, Dimethylstyrene.

If monomeric units of the second type are present, usually at least 10. wt % of the copolymer, preferably 10 to 60 wt. %, more preferably 20 to 50 wt. % of the copolymer is (at least conceptually) based on the monomeric units of the first type.

If both are present, the weight to weight ratio of first type of monomeric units to second type of monomeric units usually is in the range of 1:9 to 3:2, in particular in the range of 1:4. to 1:1.

The copolymer may comprise one or more different types of monomeric units, in addition to or alternatively to the above mentioned units of the first type and of the second type.

Preferably, the copolymer is cross-linked. This can be achieved by preparing the copolymer in the presence of a monomer or pre-polymer having two or more than two polymerisable groups (a cross-linker). The amount of cross-linker is usually 20 wt. % or less, based on total weight of the polymerisable compounds, e.g. in the range of 0.1-10 wt. %. Good results have be achieved with a crosslinker selected from the group of polyfunctional acrylates, having two or more than two polymerisable groups.

More preferably, crosslinkers are based on a monomer selected from the group of di(trimethylolpropane) tetraacrylate, trimethylolpropane triacrylate, and pentaerythritol tet- raacrylate di(trimethylolpropane) tetramethacrylate, trimethylolpropane trimethacrylate, and pentaerythritol tetramethacrylate

In a specific embodiment, the copolymer comprises monomeric units providing methanatoboron moieties. The methanotoboron moieties may be chemically bonded to the polymer as a side group or may be incorporated into the polymer chain. Providing a polymer which contains chemically bound methanatoboron moieties can be achieved by providing methanatoboron with polymerisable functionalities, such as an acrylate or methacrylate functionality, and let these take part in the polymerisation process for obtaining the organic polymer of which the sensor material at least partially consists. An advantage of having the methanatoboron moieties chemically bonded is favourable distribution throughout the material. Also it is favourable for sensor stability, as the probe is thus immobilised, thereby preventing migration or leaching of the probe.

For example, a methanatoboron derivative with a sidechain with a methacrylic group which is compatible with the polymer backbone of the organic polymer of the sensor material can be synthesised, based on a procedure reported by Sazshnikov (Nanotechnologies in Russia 7(1-2), 6-14), wherein a bromide derivative of the methanatoboron is prepared and later coupled with a tertiary amine. (Scheme 1)

Another approach is a modification to a Buchwald-Hartwig amination (Torraca et al, Journal of the American Chemical Society, 122(51), 12907-12908) reaction, by which a carbon-nitrogen bond can be created under Pd-catalyzed conditions. This procedure allows the coupling of aryl halides with amines. (Scheme 2).

If present, the monomeric unit providing the methanotoboron moiety, usually provides 0.005 to 2 wt. %, in particular 0.05 to 1 wt. % of the copolymer.

Further, in particular if the sensor material comprises nanoparticles, a further monomeric unit may be present, selected to improve dispersion of the nanoparticles. An example of such a monomeric unit is a (alkoxysilyl)alkyl (meth)acrylate, such as 3-(Trimethoxysilyl)propyl methacrylate. If present, the concentration of said dispersion improving monomeric unit usually is 1-10 wt. % of the copolymer.

As already mentioned, the sensor material may comprise one or more additives. In an advantageous embodiment, the sensor material is a composite material, comprising a dispersion of the organic polymer and nanoparticles, preferably inorganic nanoparticles. As used herein, nanoparticles are usually particles with a size in at least one dimension, preferably in three dimensions of 100 nm or less (as determined by scanning electron microscopy). The size is usually more than 5 nm in three dimensions, preferably at least 15 nm in at least one dimension, in particular at least 15 nm in three dimensions. The term 'particles' is generally used herein for substances that are in a (crystalline or amorphous) solid state at room temperature. The nanoparticles preferably are particles that contribute to the permeability or surface area. Accordingly, they are preferably nano-porous particles. The nanoparticles preferably have a hydrophobic surface, facilitating migration of the aromatic hydrocarbon into the pores. Further, a hydrophobic surface is advantageous for facilitating the homogeneous dispersion into the polymeric matrix.

The nanoparticles are preferably selected from the group of hydrophobic silica nanoparticles, hydrophobic fumed silica nanoparticles, hydrophobic silica aerogels and hydrophobic molecular sieves. Examples of hydrophobic sieves are zeolite Y silicas, mesosporous silicas, e.g. MCM-41 or SBA-15. In this respect the surface of the silica or zeolite nanoparticles is in particular considered hydrophobic if it has increased hydrophobicity compared to the unmodified silica/zeolite surface.

The molecular probe is preferably selected from the group of dibenzoylmethanatoborons, dinaphthoylmethanatoborons, di(biphenylcarbonyl)methanatoborons, naphthoyl-benzoyl methanatoborons, biphenylcarbonyl-benzoyl methanatoborons, biphenylcarbonyl-naphthoyl methanatoborons, methoxybenzoyl-benzoyl methanatoborons and methanotoboron moieties based on any of these that form part of the organic polymer, in particular dibenzoylmethanatoboron difluoride or a dibenzoylmethanatoboron difluoride moiety forming part of the organic polymer. Preferred methanoborons are represented by the following structural formulae.

-continued

Herein R1 and R2 represent the same or a different organic moiety. In an embodiment, the organic moiety is a hydrocarbon. A preferred hydrocarbon is selected from the group of alkyls, in particular C1-C6 alkyls. In a further embodiment, the organic moiety is a substituted hydrocarbon, in particular a halogenated hydrocarbon or a hydroxylated hydrocarbon. Of these alkyls comprising one or more halogen groups and hydroxy-alkyls are preferred. A substituted alkyl preferably is a C1-C6 substituted alkyl. In a further embodiment, the organic moiety comprises a polymerisable group, preferably an acrylate or methacrylate, in particular a (meth)acrylate referred to elsewhere herein.

In particular when physically distributed into the sensor material, the content of the methanatoboron usually is in the range of 0.001 to 5 wt. %, preferably is in the range of 0.05 to 1 wt. % of the total weight of the sensor material.

The sensor material (for a detector system) according to the invention usually is prepared in a method comprising
  providing one or more polymerisable compounds to be polymerised to form an organic polymer, usually a mixture comprising said one or more compounds
  carrying out a polymerisation step, thereby forming an organic polymeric material.

For providing an open-porous organic polymeric material, it is preferred to include at least one component selected open-porous nanoparticles as mentioned herein above, and removable structuring agent.

The removable structuring agent may in principle be selected from any structuring agent that can be removed from the organic polymeric material without unacceptable damage to the organic polymeric material, thereby leaving voids in the material (the open pores), once removed from the organic polymeric material. Thus, typically a structuring agent is selected that is in a different physical domain than the organic polymer for the sensor material, at least after polymerisation. For instance a salt or a sugar may be used that can be washed out with water. Advantageously, an etchable polymer is used which is phase-separated from the organic polymeric material forming (the matrix for) the sensor material. Thus a blend is formed of the structuring agent and the organic polymeric material forming (the matrix for) the sensor material. By etching the structuring agent after polymerisation, an open-porous structure is created. The methodology may be based on Myungeun Seo and Marc A. Hillmyer, *Science* 336, 1422 (2012), who describe this technique for the manufacture of materials for a different purpose.

The polymerisation may be carried out in a manner known per se, depending on the type of polymer that is to be made. For instance, radical polymerisation may be used to prepare an acrylic polymer.

The polymerisable compound is usually selected from monomers, such as those mentioned above, and pre-polymers, i.e. oligomers/polymers with at least two functional groups whereby they can be further polymerised, based on such monomers.

The molecular probe can be included before, during or after the polymerisation process. It is preferably present when polymerisation takes place if the probe is to be chemically bound to the polymer, although chemical immobilisation after polymerisation is in principle also feasible.

In a specific embodiment, inorganic nanoparticles are dispersed in an apolar liquid (such as hexane or another liquid alkane, toluene or another liquid aromatic hydrocarbon, or a cycloalkane, for instance cyclohexane). Care is taken that the nanoparticles are dispersed well to ensure no unacceptable aggregation takes place, preferably to sub-micron sized scale, and if desired aggregates are disintegrated e.g. by sonication. Thereafter the dispersion is mixed with the polymerisable compound(s), for instance using a dual asymmetrical centrifuge, after which polymerisation is commenced.

In another specific embodiment, the inorganic nanoparticles are directly mixed with the polymerisable compound(s), for instance using a dual asymmetrical centrifuge. If desired, the mixture is subjected to sonication or another technique to break nanoparticle aggregates, in order to ensure that they are dispersed well.

In an embodiment, the (mixture comprising) the polymerisable compound(s) are patterned on a substrate, before or during polymerisation. Suitable techniques include stencil printing, wire bar coating, and ink jet printing. Such techniques are generally known in the art.

The invention further relates to the use of a detector system or a sensor material according to the invention for the detection of an aromatic hydrocarbon, preferably an aromatic hydrocarbon selected from the group of benzene, toluene and xylene.

Such use generally comprises contacting at least the sensor material with a medium, generally a fluid, of which one wishes to determine whether an aromatic hydrocarbon of interest (the analyte) is present, exposing the sensor material to electromagnetic radiation of a suitable wavelength to cause fluorescence (the excitation light) if the analyte is present in the sensor material (and interacts with the probe), and measuring whether a fluorescent signal is generated (the emission light). The determination may be qualitative and/or quantitative. The fluid may in particular be a gas phase, more in particular air.

The invention will now be illustrated by the following examples.

EXAMPLE 1

Preparation of Nanoporous Membranes

The sensing material is prepared by polymerization of a monomers mixture in the presence of an etchable polymer that is initially soluble in the starting monomers mixture, but insoluble in the resulting polymer. The polymerization process is a radical polymerization process, more specifically a Reversible Addition-Fragmentation Chain Transfer process. The process requires a Chain Transfer Agent to control the chain growth of the polymer. The Chain Transfer Agent (CTA) is covalently bonded to the etchable polymer.

More specifically, the monomer mixtures consist of an aliphatic (meth)acrylic monomer, a second monomer, a crosslinking monomer and the molecular probe, with or without a polymerizable side group. The etchable polymer is polylactic acid (PLA), of a preferable molecular weight of 10 to 40 kg·mol$^{-1}$ and the chain transfer agent is a trithiocarbonate specie, preferably 2-(Dodecylthiocarbono-thioylthio)-2-methylpropionic acid.

The bonding of the CTA to the etchable polymer (PLA) follows the procedure described by Jazid Rzayev and Marc A Hillmyer. *Journal of the American Chemical Society*, 127, 13373, (2005). Briely Oxalyl chloride (0.071 mL, 8.2×10-4 moles) and 2-(Dodecylthiocarbono-thioylthio)-2-methyl-propionic acid (0.2 g, 5.5×10−4 moles) are mixed in dry CH2Cl2 (5 mL) under nitrogen atmosphere and stirred at room temperature until gas evolution stopped (~2 h). Excess reagents are then removed under vacuum, and the residue is redissolved in dry CH2Cl2 (10 mL), followed by the addition of polylactic acid (3 g in 20 mL of CH2Cl2). The reaction is allowed to proceed for 16 hours at room temperature, after which the contents are precipitated in methanol. The polymer is then redissolved in CH2Cl2, precipitated in pentane, and dried in a vacuum oven overnight. The product is the CTA terminated polylactic acid (PLA-CTA).

Typically, 30% m/m of PLA-CTA is mixed with the monomers mixture and used to create layers or monoliths of the sensing material. Typically layers of the sensing material mixture can be patterned over flat substrates by inkjet printing, stencil printing or wire bar coating. If optical fibers are used as sensing platform, the fibers can be covered by clip coating with sensing material mixture. The mixture is polymerized at 120° C. For the preparations of monoliths, a Teflon mold is used.

After polymerization, the polylactic acid (PLA) is etched by hydrolisation in an aqueous basic solution (pH~12) or by enzymatic means. The preferred enzyme is Proteinase K.

For the creation of composite materials with inorganic nanoparticles, these are added prior the polymerization of the sensor material mixture. Preferably, from 1 to 10% m/m of nanoparticles to monomer mixture is added and the mixture is performed using a dual asymmetric centrifuge. Layers are preferably prepared by stencil printing or wire bar coating.

Results

Figure 1:
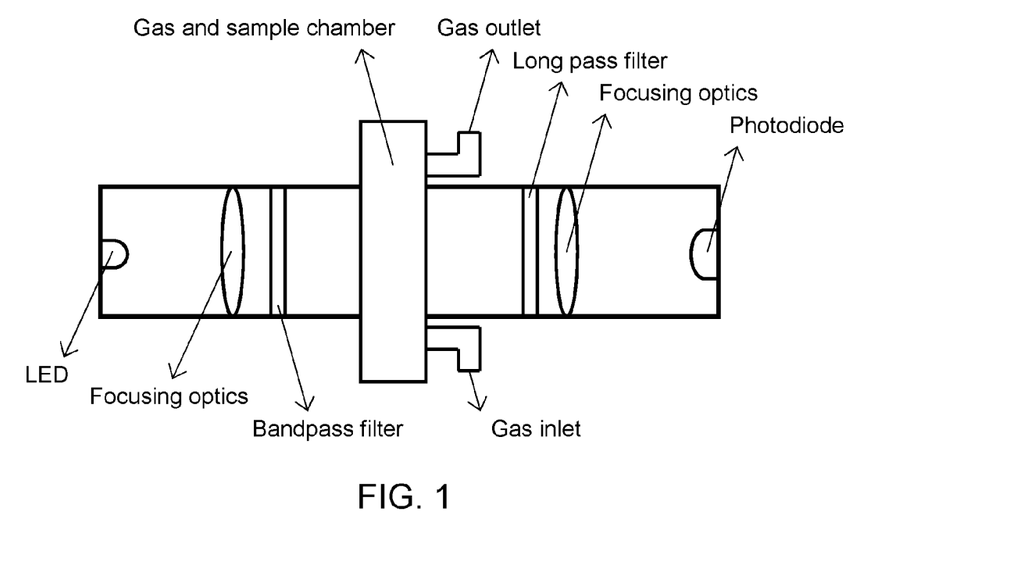
FIGS. 1 and 2 schematically show possible designs for a detection system according to the invention.
Figure 2:
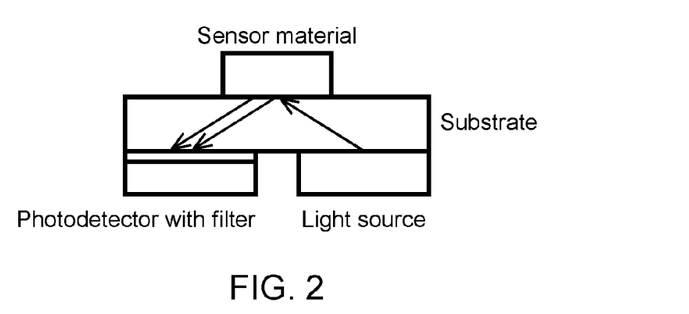
Figure 3:
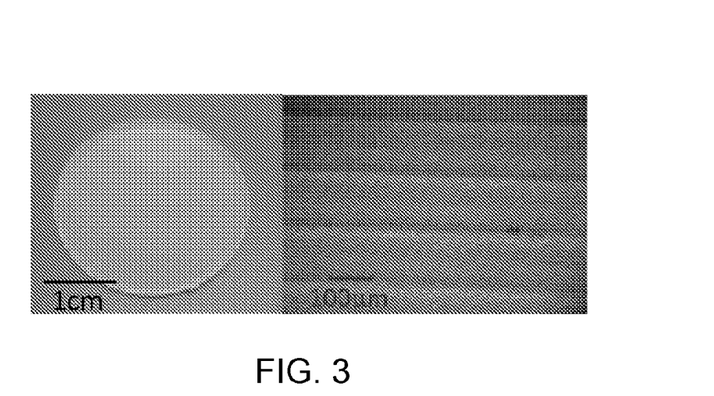
FIG. 3 shows a wire-bar coated composite of an acrylic copolymer with silica nanoparticles.

FIG. 3 shows a wire-bar coated composite of an acrylic copolymer with silica nanoparticles.

Figure 4:
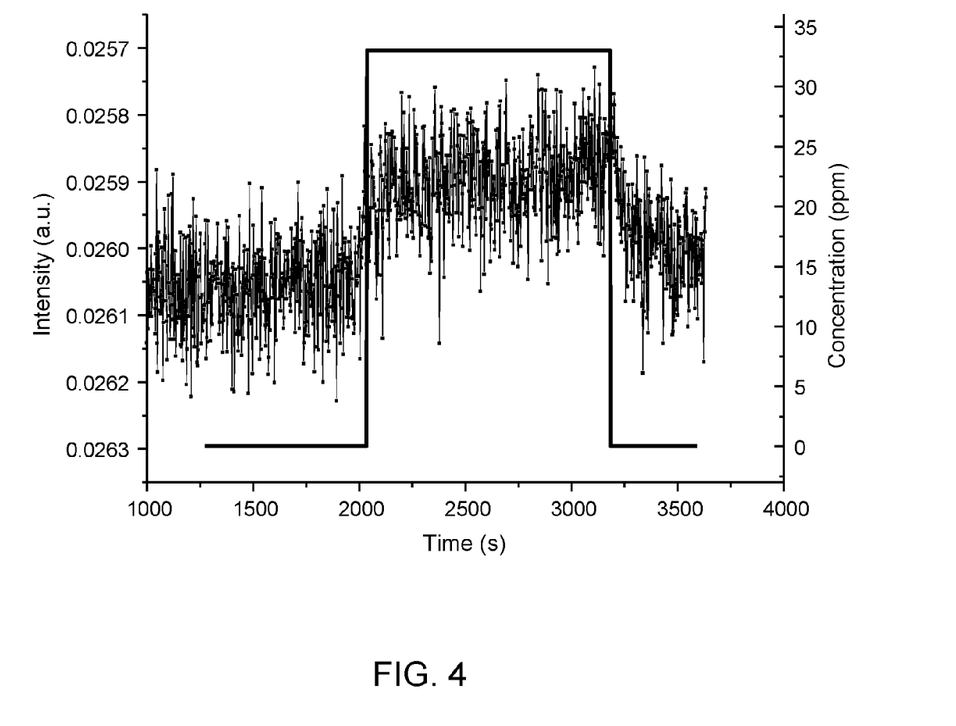
FIGS. 4, 5, 6 and 8 show fluorescent responses of a composite comprising an acrylic copolymer to toluene gas.

FIG. 4 shows a fluorescent response of a composite composed of an acrylic copolymer of lauryl acrylate and di(trimethylolpropane) tetraacrylate with silica nanoparticles, exposed to air comprising a trace of toluene. The molecular probe was dibenzoyl(methanato)boron difluoride. It was dispersed in the composite.

Figure 5:
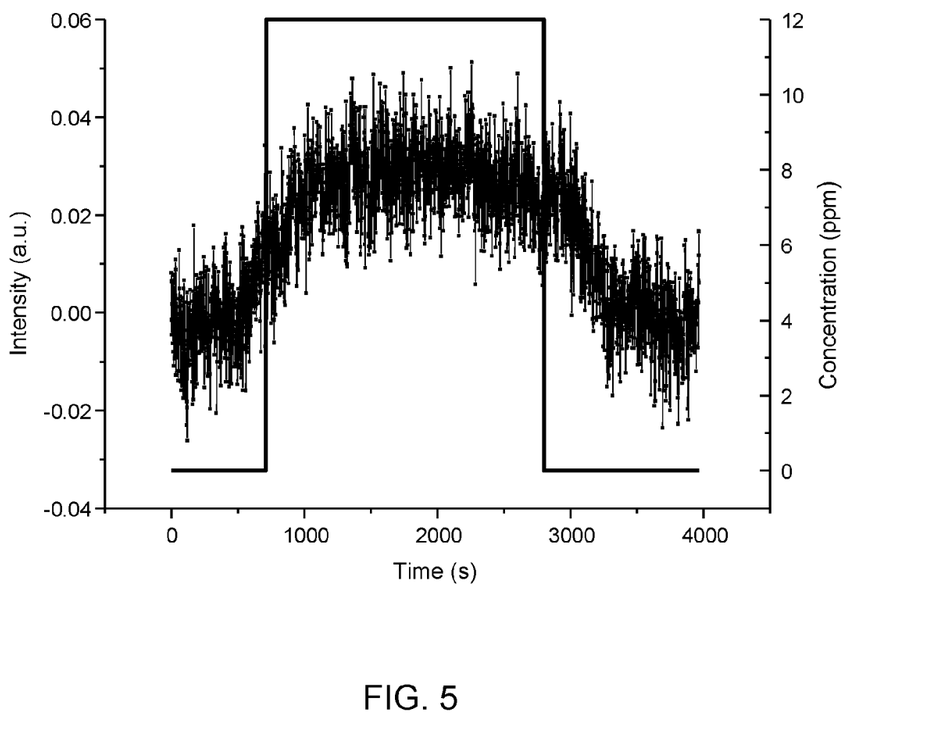

FIG. 5 shows a fluorescent response of a composite composed of an acrylic copolymer of lauryl acrylate and di(trimethylolpropane) tetraacrylate with aerogel particles to a stream of toluene gas.

Figure 6:
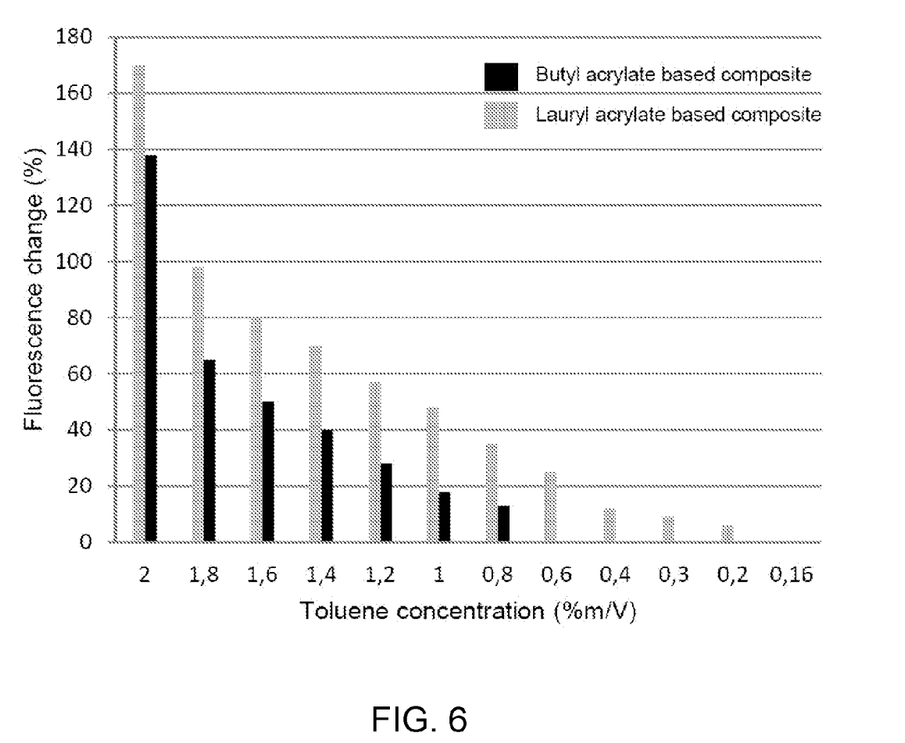
Figure 7:
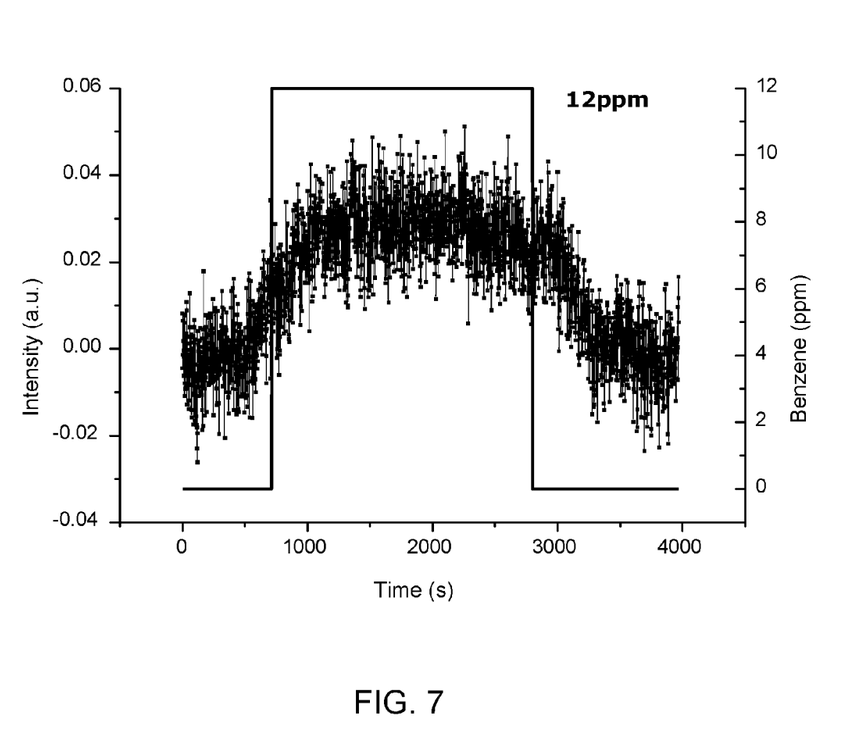
FIG. 7 shows a fluorescent response to benzene.

FIG. 6 shows a fluorescent response of two acrylic formulations with silica nanoparticles to a stream a gas toluene. One is butyl acrylatecoplolymer based composite and the other a lauryl acrylate copolymer based composite. The co-monomers in both of the copolymers were di(trimethylolpropane) tetraacrylate and trimethylsilyl acrylate). The composition of the butyl based: 75% m/m Butyl acrylate, 18% m/m di(trimethylolpropane) tetraacrylate, 7% trimethylsilyl acrylate. The composition of the lauryl based: 82% m/m Lauryl acrylate, 11% di(trimethylolpropane) tetraacrylate, 7% trimethylsilyl acrylate FIG. 7 shows the fluorescent response when exposed to benzene of a sensor, wherein the sensor material was di(t-rimethylolpropane) tetraacrylate 80% wt/wt, silica nanoparticles (10 nm diameter) 20% wt/wt.

EXAMPLE 2

Figure 8:
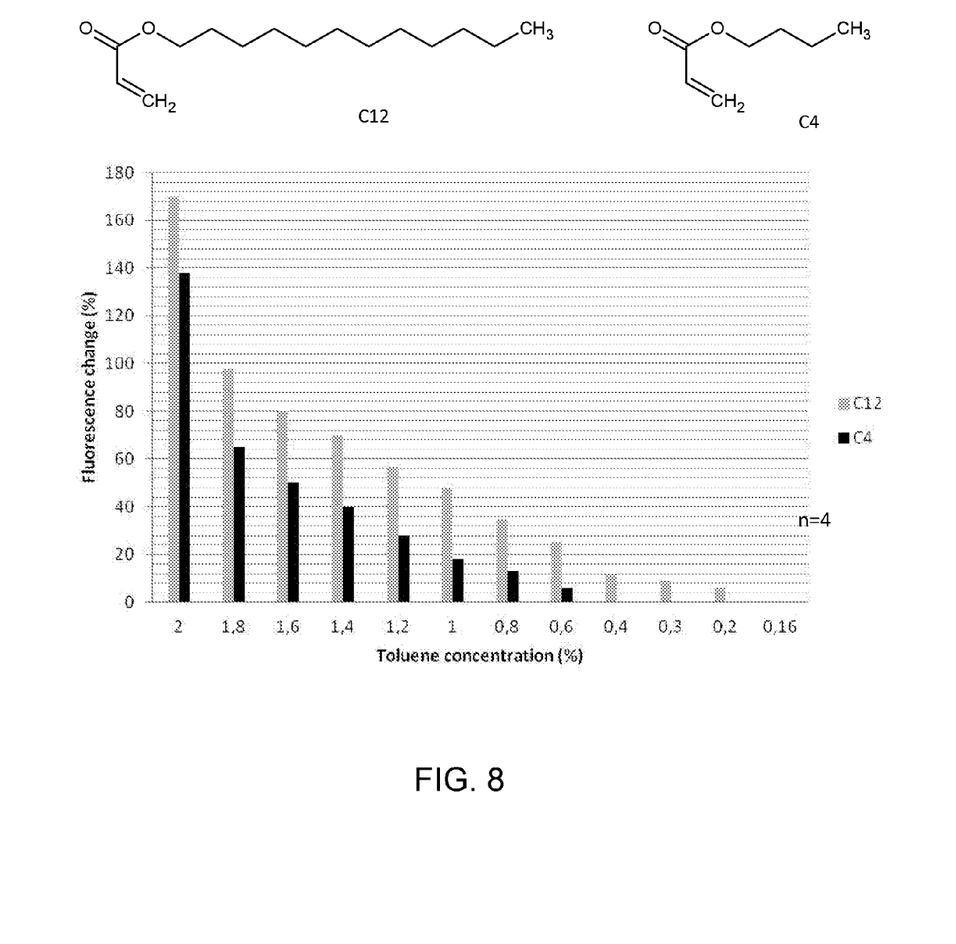

Example 1 was repeated with the following modifications: films were produced by drop casting acrylate precursor. FIG. 8 shows FIG. 6 shows a fluorescent response of two acrylic formulations with silica nanoparticles to a stream a gas toluene. One is butyl acrylatecoplolymer based composite and the other a lauryl acrylate copolymer based composite. The co-monomers in both of the copolymers were di(trimethylolpropane) tetraacrylate and trimethylsilyl acrylate). The composition of the butyl based: 75% m/m Butyl acrylate, 18% m/m di(trimethylolpropane) tetraacrylate, 7% trimethylsilyl acrylate.

The composition of the lauryl based: 82% m/m Lauryl acrylate, 11% di(trimethylolpropane) tetraacrylate, 7% trimethylsilyl acrylate.

The invention claimed is:

1. Detector system suitable for detection of an aromatic hydrocarbon, comprising an organic polymeric sensor material that is open-nanoporous and permeable to the aromatic hydrocarbon wherein the pore volume of said sensor material is 0.2-0.5 ml/g and wherein, the sensor material contains a molecular probe, which probe is a methanatoboron moiety.

2. Detector system according to claim 1, wherein the organic polymeric sensor material comprises a copolymeric matrix polymer, formed of at least two different monomeric units.

3. Detector system according to claim 2, and wherein at least one of the monomeric units is based on a chain-packaging-reducing monomer.

4. Detector system according to claim 3, and wherein the chain-packaging-reducing monomer is a (meth)acrylic monomer or a functionalised styrene monomer.

5. Detector system according to claim 2, wherein at least one of the monomeric units is based on an aliphatic monomer.

6. Detector system according to claim 5, wherein the aliphatic monomer is based on an aliphatic acrylate.

7. Detector system according to claim 6, wherein the aliphatic acrylate is based on: n-butyl acrylate, isobutyl acrylate, n-pentyl acrylate, n-hexyl acrylate, n-heptyl acrylate, n-octyl acrylate, isooctyl acrylate.

8. Detector system according to claim 2, wherein the organic polymeric sensor material comprises a copolymeric matrix polymer formed of at least two different monomeric units and a crosslinker.

9. Detector system according to claim 1, wherein the molecular probe forms part of a polymeric molecule.

10. Detector system according to claim 1, wherein the molecular probe is selected from the group of dibenzoylmethanatoborons, naphthoyl-benzoyl methanatoborons, biphenylcarbonyl-benzoyl methanatoborons, biphenylcarbonyl-naphthoyl methanatoborons, methoxybenzoyl-benzoyl) methanatoborons and methanotoboron moieties based on any of these that form part of the organic polymer.

11. Detector system according to claim 10 wherein the molecular probe is dibenzoylmethanatoboron difluoride or a dibenzoylmethanatoboron difluoride moiety forming part of the organic polymer.

12. Detector system according to claim 1, wherein the sensor material is a membrane.

13. Detector system according to claim 1, wherein the detector system is an optical read-out platform comprising the sensor material patterned on a surface of the platform.

14. An organic polymeric sensor material that is open-nanoporous and permeable to aromatic hydrocarbons wherein the pore volume of said sensor material is 0.2-0.5 ml/g and wherein, the sensor material contains a molecular probe, which probe is a methanatoboron moiety.

15. Method for preparing the sensor material of claim 14, comprising (a)—providing a mixture comprising one or more polymerisable compounds to be polymerised to form an organic polymer and at least one component which is a removable structuring agent;
(b)—subjecting the mixture to polymerisation, under formation of a blend of the organic polymer and the removable structuring agent;
(c)—thereafter removing the removable structuring agent, thereby forming the nanoporous organic polymeric material; and
wherein said molecular probe is added before, during or after conducting steps (a), (b) and (c); or
wherein said molecular probe is a methanatoboron moiety coupled to said polymerizable compound.

16. Method according to claim 15, wherein the mixture is patterned on a substrate, before or during polymerisation.

17. A method to detect an aromatic hydrocarbon which comprises providing to an environment to be tested with the detector system according to claim 1 or a sensor material according to claim 14.

18. The method according to claim 17, wherein the aromatic hydrocarbon is benzene.

19. The method according to claim 17, wherein the aromatic hydrocarbon is toluene.

20. The method according to claim 17, wherein the aromatic hydrocarbon is xylene.

21. The method according to claim 17, wherein the aromatic hydrocarbon is in a gas phase.

22. The method according to claim 21, wherein the gas phase is air.

23. The sensor material of claim 14 wherein the molecular probe forms part of a polymeric molecule.

* * * * *